(12) United States Patent
Zerbe et al.

(10) Patent No.: US 8,691,272 B2
(45) Date of Patent: Apr. 8, 2014

(54) MULTILAYER TABLET

(75) Inventors: Horst G. Zerbe, Hudson (CA); Nadine Paiement, Montreal (CA); Pompilia Lspas-Szabo, Greenfield Park (CA)

(73) Assignee: Intelgenx Corp., St. Laurent, Quebec (CA)

( * ) Notice: Subject to any disclaimer, the term of this patent is extended or adjusted under 35 U.S.C. 154(b) by 2223 days.

(21) Appl. No.: 11/647,033

(22) Filed: Dec. 28, 2006

(65) Prior Publication Data

US 2007/0190144 A1 Aug. 16, 2007

Related U.S. Application Data

(60) Provisional application No. 60/755,280, filed on Dec. 30, 2005.

(51) Int. Cl.
*A61K 9/26* (2006.01)
(52) U.S. Cl.
USPC .......................................................... 424/470
(58) Field of Classification Search
None
See application file for complete search history.

(56) References Cited

U.S. PATENT DOCUMENTS

| | | | |
|---|---|---|---|
| 3,851,648 A | 12/1974 | Brooke | |
| 4,662,880 A * | 5/1987 | Hamel et al. | 424/467 |
| 4,792,452 A | 12/1988 | Howard et al. | |
| 4,839,177 A | 6/1989 | Colombo et al. | |
| 4,871,549 A | 10/1989 | Ueda et al. | |
| 4,957,745 A | 9/1990 | Jonsson et al. | |
| 5,081,154 A | 1/1992 | Appelgren et al. | |
| 5,169,638 A | 12/1992 | Dennis et al. | |
| 5,342,627 A | 8/1994 | Chopra et al. | |
| 5,391,377 A | 2/1995 | Barnwell | |
| 5,399,358 A | 3/1995 | Baichwal et al. | |
| 5,399,362 A | 3/1995 | Baichwal et al. | |
| 5,422,123 A | 6/1995 | Conte et al. | |
| 5,601,842 A * | 2/1997 | Bartholomaeus | 424/464 |
| 5,783,212 A | 7/1998 | Fassihi et al. | |
| 5,853,760 A | 12/1998 | Cremer | |
| 6,254,886 B1 | 7/2001 | Fusca et al. | |
| 6,309,668 B1 * | 10/2001 | Bastin et al. | 424/472 |
| 6,558,701 B2 | 5/2003 | Bartholomaeus et al. | |
| 6,797,283 B1 | 9/2004 | Edgren et al. | |
| 6,960,357 B2 | 11/2005 | Chopra | |

FOREIGN PATENT DOCUMENTS

| | | |
|---|---|---|
| CA | 2 137017 | 5/1995 |
| CA | 2 197941 | 8/1997 |
| WO | WO 98/30208 | 7/1998 |
| WO | WO 2004/064815 | 8/2001 |

\* cited by examiner

*Primary Examiner* — David J Blanchard
*Assistant Examiner* — Tigabu Kassa
(74) *Attorney, Agent, or Firm* — Butzel Long

(57) ABSTRACT

A multilayer oral dosage form that provides controlled release of an active compound includes a non-erodible core containing a pharmaceutically active compound and/or a nutritionally active compound, and at least one release-modulating layer laminated to each side of the core layer. The dosage form can be prepared using simple, inexpensive tablet compression techniques.

1 Claim, 3 Drawing Sheets

MULTILAYER TABLET

CROSS-REFERENCE TO RELATED APPLICATION

This application claims priority under 35 U.S.C. §119(e) on U.S. Provisional Application No. 60/755,280 entitled MULTILAYER TABLET, filed Dec. 30, 2005, the entire disclosure of which is incorporated herein by reference.

FIELD OF THE INVENTION

This invention relates to oral dosage forms for the delivery of pharmaceutically and/or nutritionally active compounds, and more particularly to multilayer tablets that are formulated to provide controlled release of an active compound.

BACKGROUND OF THE INVENTION

Multilayered tablets, including trilayer tablets, have been used to modulate the release of an active compound, to increase absorption and bioavailability of an active compound, to deliver fixed-drug combinations, to provide a physical barrier between incompatible substances, and to mask unpleasant taste.

U.S. Pat. No. 5,342,627 discloses a device for the release of at least one active substance into a fluid medium by dissolution of the active substance in the medium, wherein the device comprises a covering that is impermeable to the active substance and the fluid medium and which has at least one aperture defining a shaped cavity filled by a core containing the active substance. The geometry of the device is selected to maintain a constant surface area of exposed active substance for a significant period to achieve a constant release of active substance over that period.

U.S. Pat. No. 6,960,357 discloses a controlled release dissolution and diffusion device which can deliver an active ingredient at a constant or controlled-variable rate. The device comprises an active ingredient and dissolution modifiers and/or an insoluble matrix.

The matrix is coated, except for at least one exposed face, with a coating containing an insoluble polymer or a mixture of an insoluble polymer and pore-forming elements. The delivery device is said to produce linear (zero-order) kinetics for releasing a chemical compound over a desired period. The disintegration rate of the coating can be manipulated by changing the concentration and/or size of the pore-forming materials, the water solubility of the materials, and/or the thickness and composition of the coating.

U.S. Pat. No. 5,853,760 discloses a device for controlling the release of an active substance in a liquid media from an active substance-containing matrix. The device includes exposed matrix surfaces for releasing the active substance, and surfaces that are covered by an erodible mass of solids. The use of thickness gradients is said to provide an erodible mass that is eroded at a rate intended to effect an enlargement of the contact surface of the active substance-containing matrix.

SUMMARY OF THE INVENTION

It has been discovered that an inexpensive, easily manufactured controlled release solid oral dosage form can be achieved utilizing a trilayer tablet structure which includes a non-erodible core containing at least one pharmaceutically active compound and/or at least one nutritionally active compound, and at least one erodible release-modulating layer laminated to each side of the non-erodible core layer.

The resulting dosage form is a diffusion-controlled device that contains a pharmaceutically or nutritionally active compound distributed through an insoluble matrix that remains substantially intact during release of the drug. As the drug becomes depleted from the matrix in the proximity of the exposed surface, the drug release rate becomes a function of diffusion path length through the insoluble matrix. The invention provides a viable solution for delivering pharmaceutically active compounds and/or nutritionally active compounds using a cost-efficient technology.

These and other features, advantages and objects of the present invention will be further understood and appreciated by those skilled in the art by reference to the following specification.

DESCRIPTION OF PREFERRED EMBODIMENTS

Figure 6:
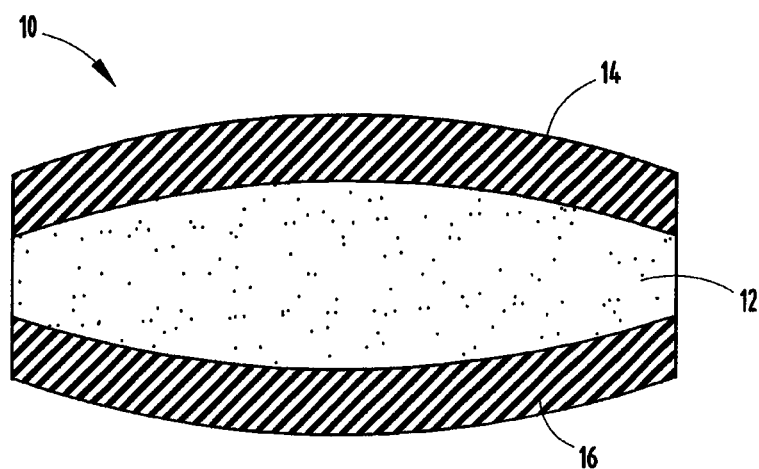
FIG. 6 is a cross section view of a trilayer tablet in accordance with the invention.

As shown in FIG. 6, the multilayer tablets 10 of this invention comprise at least three layers, including a non-erodible layer 12 that does not change dimensions during use, and which is sandwiched between at least two additional layers 14, 16, at least one of which is laminated to each of two opposite sides of the non-erodible layer. The dosage form is intended to provide a cost-efficient alternative for linear or quasi-linear (nearly linear) release of at least one active compound.

The expression "trilayer tablet" encompasses tablets consisting of only three layers, as well as tablets comprising these three layers and at least one additional layer. For example, the expression "trilayer tablet" encompasses a tablet having a non-erodible layer sandwiched between two additional layers, on to which an aesthetic or functional coating, and/or one or more additional layers may be added.

The expression "non-erodible layer" means that there is substantially no disintegration or dissolution of the matrix material of the non-erodible layer within the gastrointestinal tract, or at least through the portion of the gastrointestinal tract where the active compound is intended to be released. In contrast, the expression "controlled erosion" refers to erosion of a layer at a gradual predetermined rate during transit of a dosage form through the gastrointestinal tract. Erodible and non-erodible materials are well known in the pharmaceutical arts.

Active compounds that may be incorporated into the dosage forms of the invention include generally any pharmaceutically active compounds and/or nutritionally active compounds which can be administered orally, and which have a therapeutic effect. The pharmaceutical dosage forms of this invention may be used for delivery of generally any pharmaceutically active compound, but are most advantageously employed with soluble pharmaceutically active compounds, especially the more highly soluble pharmaceutically active compounds. The term "soluble" refers to a compound that is capable of dissolving in gastrointestinal fluids, including gastric juices and/or intestinal juices.

Nutritionally active compounds include various vitamins and minerals, as well as other nutrients, which could also have a therapeutic effect. Thus, there are some active compounds that could be regarded as being both pharmaceutically active and nutritionally active, in some cases depending on the dose.

Other examples of pharmaceutically active compounds that may be advantageously employed in the dosage forms of this invention include cannabidiol and tetrahydrocannabinol.

The term "laminated" refers to one layer being joined to or united with another layer, such as by sequential compression steps which join different layers together to form a single dosage form, in which the individual layers will not separate from one another during normal use (i.e., during its residence in a gastrointestinal tract of a mammal), other than by a gradual disintegration or dissolution of an erodible layer laminated to the non-erodible core layer.

The term "insoluble," as used to describe polymer excipients, refers to a material that does not dissolve within the gastrointestinal tract, or at least not within a portion of the gastrointestinal tract targeted for delivery of the pharmaceutically and/or nutritionally active compound. The term "non-swellable" as used to describe polymer excipients refers to a material that is substantially incapable of imbibing fluid and expanding when in contact with fluid present in the environment of use, i.e., within the gastrointestinal tract. The term "swellable," as used to describe polymer excipients, refers to materials that are capable of imbibing fluid and expanding when in contact with fluid present in the environment of use, i.e., the gastrointestinal tract.

The non-erodible core comprises a polymer matrix in which a pharmaceutically active compound and/or a nutritionally active compound is distributed, typically uniformly. The polymers comprising the non-erodible core may consist exclusively of one or more insoluble polymers defining a porous matrix, or a combination of one or more non-swellable insoluble polymers and one or more swellable insoluble polymers. As another alternative, the non-erodible core may be comprised of an insoluble polymer, a pharmaceutically active compound and/or a nutritionally active compound, and pore-forming materials that, along with the pharmaceutically or nutritionally active compound, are distributed within the polymer matrix.

Pore-forming materials include materials that dissolve, erode or leach out of the non-erodible core leaving pores. Examples include alkali and alkaline earth metal salts; mono-, di- and polysaccharides; and organic aliphatic alcohols, including diols, polyols; polyhydric alcohol, polyalkylene glycol, polyglycol, alpha, omega-alkylene diols. Preferred pore-forming materials including sugars such as lactose, dextrose, fructose, glucose; polysaccharides such as dextran; and polyols such as sorbitol, propylene glycol, and glycerin.

Examples of non-swellable insoluble polymers that may be utilized in preparing the non-erodible core layer include ethyl cellulose, polyvinyl acetates, and methacrylic copolymers.

Suitable swellable insoluble polymers that may be utilized in preparing the non-erodible core layer include hydroxypropylmethyl cellulose, hydroxypropyl cellulose, polyvinylpyrrolidone, polyethylene oxides, and modified starches. Typically, when a combination of a non-swellable insoluble polymer and a swellable insoluble polymer is used for forming the non-erodible core layer, the non-swellable insoluble polymer or polymers comprise from about 5 to about 20% by weight of the core layer and the swellable insoluble polymer or polymers comprise up to about 10% by weight of the core layer, with the balance of the core comprising water-soluble polymers, the pharmaceutically active compound and/or nutritionally active compound, and any desired lubricants, and other excipients and/or adjuvants.

The outer layers sandwiching the non-erodible core layer may be comprised of swellable erodible polymers, water permeable erodible polymers, or erodible polymers that are insoluble in gastrointestinal fluids, or a combination of these polymers. These sandwiching layers 14 and 16 may contain one or more pharmaceutically or nutritionally active compounds, that may be the same or different from that of the core layer 12.

The materials comprising the non-erodible core layer and/or the layers laminated to the non-erodible core layer may further comprise fillers, plasticizers, flowability enhancers, disintegrants, compression agents, etc., depending on the dosing requirements of the particular active compound or compounds.

The trilayer tablets of this invention may be prepared by first granulating at least one active compound with a swellable polymer such as hydroxypropyl cellulose. The granules may be prepared by a wet granulation process using water as a granulation solution. This procedure involves creating a homogeneous mixture of the active and the swellable polymer (e.g., hydroxypropyl cellulose), such as in a DIOSNA mixer bowl, wherein the mixer and chopper motors are set at appropriate rotational speeds, such as 500 rpm and 1,000 rpm, respectively. The wet granulates may be passed through a sieve (e.g., a 2.36 millimeter mesh size), dried, such as at 50° C. for 30 minutes, and passed through a second sieve (e.g., 0.85 millimeter mesh size), and subsequently oven dried to a suitable residual moisture level (e.g., typically less than 2%). The resulting dry, sieved granules may then be distributed in a polymer matrix by mixing the dry granules with suitable polymers (e.g., Kollidon SR and Methocel K100) that have been previously passed through a sieve (e.g., a 0.60 millimeter mesh sieve). Any desired excipients may be mixed in with the matrix polymers and granules, such as by using an Inversina mixer for an appropriate period (e.g., 5 minutes), and thereafter adding a lubrication agent and mixing for an additional appropriate period (e.g., about one minute). The resulting mixture may be compressed into a core that is inserted into a die and disposed between layers of material that form the outer erodible layers for final compression into a trilayer tablet form. Alternatively, the mixture of matrix polymers, granules containing an active compound and optional excipients may be deposited in a loose (non-precompressed) form onto a layer of material that forms one of the erodible layers, in a layer by layer sequential tablet compression technique as described below. A suitable final tablet diameter is about 10.8 millimeters, and a suitable hardness for the core layer is about 8.0 kP.

A trilayer tablet in accordance with the invention may be manufactured by filling a first layer composition (one of the two layers laminated to the non-erodible core layer) into the bottom of the die, applying a light compression force for compaction of the layer, filling the second layer (i.e., the non-erodible core layer), followed by light compression. Finally, the third layer (the second layer laminated to the non-erodible core layer) is added on top of the existing two layers and the entire content of the die is subjected to an optimal compression force by the die punches inserted into the die so that a tablet is formed. This procedure eliminates difficulties of core insertion into the die which is required for core/mantle tablets or for conventional multilayer tablets having a layer represented by a pre-compressed core, thereby simplifying the manufacturing process.

When the multilayer tablets of the invention are in contact with aqueous media or physiological fluids (e.g., gastrointestinal fluids), the water penetration will induce various physical changes in each of the layers. At least one composition will become a plastic non-erodible layer by in-situ formation of a polymeric matrix. In dry phase, the tablet may have a homogeneous aspect, without any visually distinct layers. At hydration, the behavior of each layer changes and, depending on its composition, may have a different functionality.

Release of the active compound from the dosage form is dependent on the diffusion path length which increases during passage of the dosage form through the gastrointestinal tract, and permeability of the erodible layers, which increases during passage through the gastrointestinal tract. The materials and thicknesses of the layers may be selected to achieve a substantially constant rate of release.

Various combinations of layers and selected pharmaceutical excipients could be used to modulate the active substance release profiles depending on drug solubility, loading or therapeutical needs.

The tablets of this invention may be manufactured using processes that avoid costly manufacturing steps, such as two-step compression, pre-compression of cores in a separate manufacturing operation, and subsequent placement of such cores in a die using slow and expensive core-transfer techniques. Accordingly, the invention provides a simple, cost-efficient technique for providing a wide range of controlled release drug delivery systems for a wide range of applications in the pharmaceutical and nutritional market.

The invention will be further illustrated by the following examples, which are intended to illustrate, but not limit the scope of the invention.

The present invention provides multiple layer extended or controlled release oral dosage forms where at least one of the layers contains an active substance incorporated in a non-erodible matrix.

EXAMPLE 1

This example provides types of formulations for the non-erodible core consisting of active drug, matrix-forming polymer, controlled release agent(s), suitable diluent/binder, glidants and optional lubricants.

The active substance may be incorporated in the dosage form as a premix with suitable excipients exhibiting hydrophilic or hydrophobic characteristics such as stabilizers, pH dependent or independent swelling and/or erodible release modifying agents, binders or diluents. Such premix could be obtained by granulation with solvents including water, alcoholic solutions or other volatile solvent preparations. Granules obtained are dried and blended with release-control agents, matrix-forming polymers, optional binders, glidants and lubricants.

The preparation of core layer formulations consists of dry mixing insoluble polymers together with a granulation containing the active compound(s). The granulation may contain a swellable polymer, flowability enhancers, compressibility enhancers, etc. Insoluble polymers may be selected from one of the categories: ethylcellulose, polyvinyl acetates, methacrylic copolymers, etc while swellable polymers are represented by hydroxyypropylmethyl cellulose derivatives (HPMC), hydroxypropyl cellulose, polyvinyl pyrrolidone, modified starches, polyethylene oxides, etc.

The proposed formulations for core layer could afford high loading, up to at least about 50% for highly soluble drugs (Table I). The major component of the core layer is represented by one insoluble polymer or a mixture of two insoluble polymers (between 30 to 60% from the total mass of the core layer) to ensure the robustness of the drug delivery systems associated with controlled release properties. Selected swellable polymers may also be used in the mixture as release barriers but their presence is in small proportions (between 1 to max 10%).

TABLE I

| Components | Core 1 (%) | Core 2 (%) | Core 3 (%) |
|---|---|---|---|
| Active substance | 45 | 50 | 36 |
| Functional polymer blend* | 44 | 34 | 58 |
| Swellable polymer type A (low hydration rate) | 10 | — | — |
| Swellable polymer type B (high hydration rate) | — | 2 | 5 |
| Ethyl cellulose derivative | — | 13 | — |
| Lubricant | 1 | 1 | 1 |

*Blend of soluble and insoluble polymers, e.g., polyvinyl acetate and polyvinylpyrrolidone.

All formulations are presented in percentage of weight.

The active substance could be one of highly soluble drugs such as metoprolol salt, Tramadol HCl, Bupropion, Propanolol, etc.

EXAMPLE 2

This example provides types of extended release formulations suitable for controlled erosion layers which can be any combination of the following pharmaceutical acceptable excipients: a) swelling and erodible polymers; b) insoluble polymers c) water permeable polymers, alone or in combination with selected diluents/binders.

All formulations are presented in percentage by weight and can be obtained by dry mixing of the corresponding powders.

An optimal ratio between polymers exhibiting hydrophilic/hydrophobic characteristics that are reflected in swelling and/or permeability properties will ensure a controlled erosion of these layers. The compositions incorporate between 10 and 30% of an insoluble polymer, more preferable between 15 to 25% in a ratio of from about 1:2 to about 2:1 with a water permeable polymer (Table II). The formulation may also contain swellable polymers selected from cellulose derivatives depending on their molecular weight and degree of substitution.

Low viscosity grades exhibiting rapid hydration are preferred. The ratio between these two classes is from about 1:2 to about 2:1. Optional glidants and lubricants could also be used.

TABLE II

| Component | Cover A | Cover B | Cover C |
|---|---|---|---|
| Insoluble polymer | 16 | 18 | 20 |
| Water permeable polymer | 16 | 18 | 17 |
| Swellable polymer | 27 | 33 | 38 |

TABLE II-continued

| Component | Cover A | Cover B | Cover C |
|---|---|---|---|
| (slow hydration rate) | | | |
| Swellable polymer (low viscosity) | 38.5 | 28.5 | 22.5 |
| Glidant | 2 | 2 | 2 |
| Lubricant | 0.5 | 0.5 | 0.5 |

EXAMPLE 3

Figure 1:
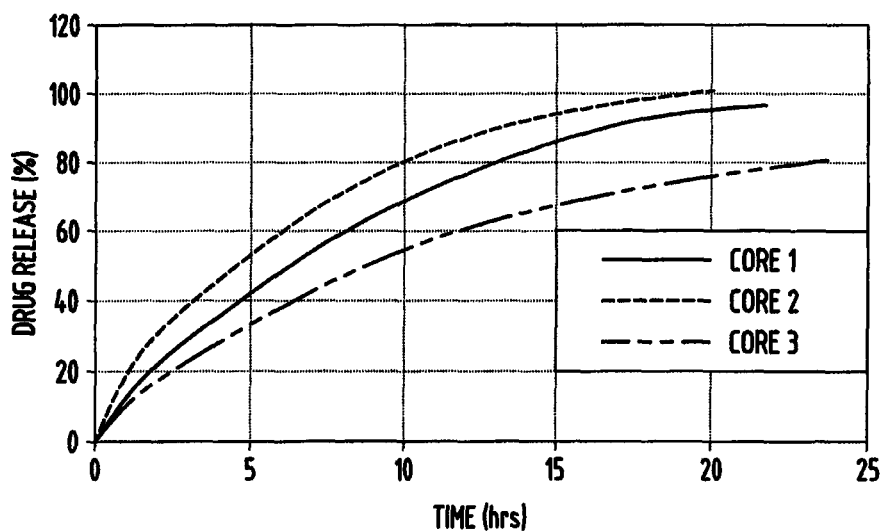
FIG. 1 is a graph showing the in vitro dissolution profiles for trilayer tablets in accordance with the invention as described in Example 3.

This example provides a combination of two types of formulation that can generate a trilayer tablet ensuring the controlled release of highly soluble drugs from high loaded tablets. The system represents a multilayer tablet proposed as a dosage for once-a-day administration. Depending on selection of hydrophilic/hydrophobic characteristics of excipients and on their swelling/erodible properties various release profiles could be generated. Dissolution tests in vitro have shown that the proposed system can ensure a linear kinetic profile for up to 20 hours. FIG. 1 illustrates the capacity of a trilayer tablet to modulate the release of highly soluble drug from a once-a-day administration dosage form by various modifications of core layer compositions (in vitro kinetic profiles corresponding to three different CORE formulations associated to the same cover layer composition).
Multilayer tablets consisting in:

| Layer 1 | Erodible placebo layer (formulation cover A) |
| Layer 2 | Drug containing core (formulation CORE 1) |
| Layer 3 | Erodible placebo layer (formulation cover A) |

Multilayer tablets consisting in:

| Layer 1 | Erodible placebo layer (formulation cover A) |
| Layer 2 | Drug containing core (formulation CORE 2) |
| Layer 3 | Erodible placebo layer (formulation cover A) |

Multilayer tablets consisting in:

| Layer 1 | Erodible placebo layer (formulation cover A) |
| Layer 2 | Drug containing core (formulation CORE 3) |
| Layer 3 | Erodible placebo layer (formulation cover A) |

EXAMPLE 4

Figure 2:
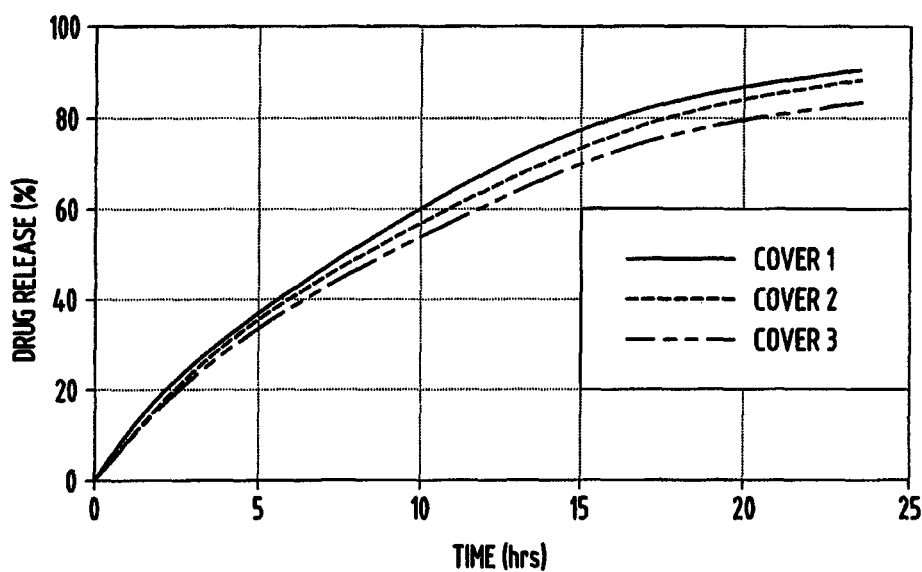
FIG. 2 is a graph showing in vitro dissolution profiles for trilayer tablets in accordance with the invention as described in Example 4.

This example provides a combination of two types of formulation that can generate a trilayer tablet ensuring the controlled release of highly soluble drugs from high loaded tablets.
The system represents a multilayer tablet for once-a-day administration. Depending on selection of hydrophilic/hydrophobic characteristics of excipients and on their swelling/erodible properties various release profiles could be generated. Dissolution tests in vitro have shown that the proposed system can ensure a linear kinetic profile for up to 20 hours. FIG. 2 illustrates the capacity of a trilayer tablet to modulate the release of highly soluble drug from a once-a-day administration dosage form by various modifications of cover layer formulations (in vitro kinetic profiles corresponding to three different cover formulations associated to the same CORE layer composition).
Multilayer tablets consisting in:

| Layer 1 | Erodible placebo layer (formulation cover B) |
| Layer 2 | Drug containing core (formulation CORE 1) |
| Layer 3 | Erodible placebo layer (formulation cover B) |

Multilayer tablets consisting in:

| Layer 1 | Erodible placebo layer (formulation cover C) |
| Layer 2 | Drug containing core (formulation CORE 1) |
| Layer 3 | Erodible placebo layer (formulation cover C) |

Examples 1, 3 and 4 represent multilayer tablets obtained with metoprolol succinate.

EXAMPLE 5

Figure 3:
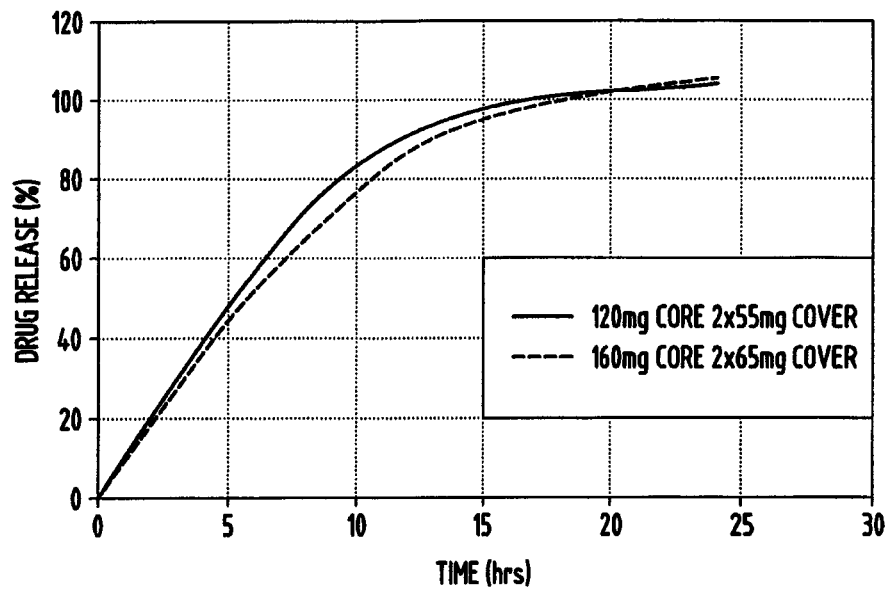
FIG. 3 is a graph showing in vitro dissolution profiles of Propanolol for trilayer tablets in accordance with the invention as described in Example 5.

This example illustrates the same concept of multilayer system applied to another highly soluble active molecule, i.e. Propanolol (FIG. 3). It was shown that the proposed system is extremely versatile and easy to adjust to various molecules.

EXAMPLE 6

Figure 4:
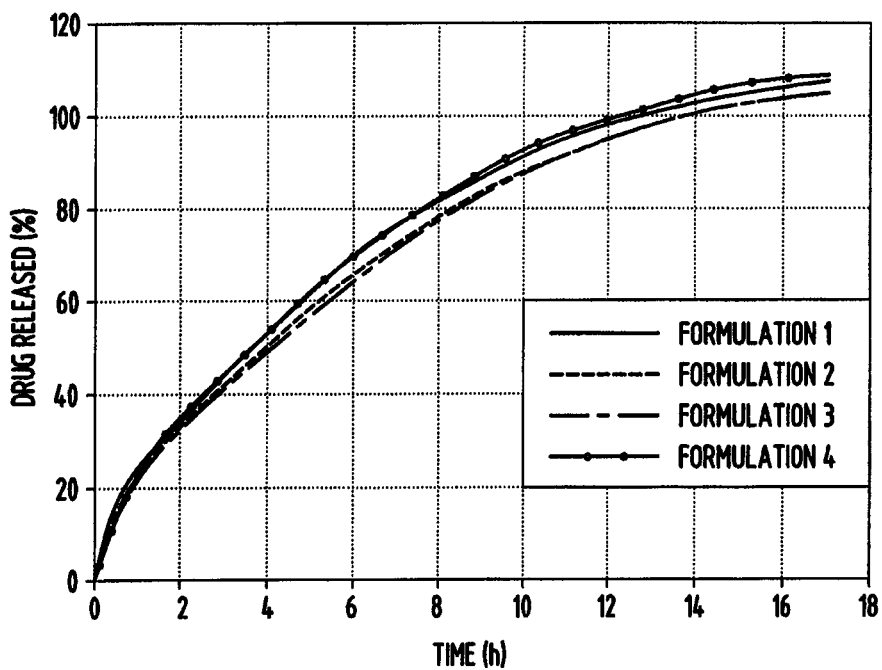
FIG. 4 is a graph showing in vitro dissolution profiles for trilayer tablets in accordance with the invention as described in Example 6.

This example provides a trilayer tablet ensuring the controlled release of highly soluble drugs from high loaded tablets that also exhibit gastro-retentive properties. FIG. 4 presents the metformin release profile in vitro from such a multilayer system.

EXAMPLE 7

Figure 5:
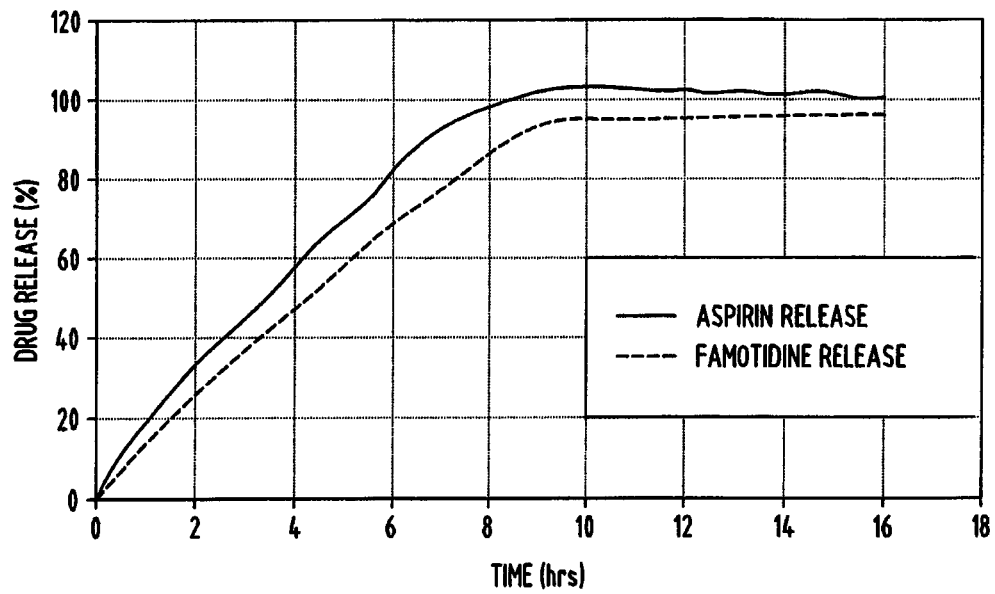
FIG. 5 is a graph showing in vitro dissolution release profiles from a fixed dose combination trilayer tablet in accordance with the invention as described in Example 7.

This example represents the application of the proposed invention for preparation of fixed-dose combination tablets. Using the proposed trilayer system, a combination of a non-steroidal anti-inflammatory drug (NSAID) and $H_2$-bloker could be obtained for a once-a-day dosage form (FIG. 5). Such tablet could ensure the controlled release of the NSAID, thereby protecting the stomach mucosa.

EXAMPLE 8

A specific example of cannabidiol dosage form prepared in accordance with the invention has the following core and erodible outer layers (cover layers) formulas: Core and Cover Layer Formulation for Trilayer Tablet of 700 mg Cannabinodiol

| | (mg) | % |
|---|---|---|
| Core | | |
| API, Cannabidiol | 500 | 62.5 |
| Polaxamer[1] | 80 | 10 |
| Polysorbate | 8 | 1 |
| Kollidon SR[2] | 176 | 22 |
| Polyethylene oxide (2M) | 24 | 3 |
| Silicon dioxide | 8 | 1 |
| Mg stearate | 4 | 0.5 |
| Sub weight | 800 mg | |

| | (mg) | % |
|---|---|---|
| Cover layer | | |
| API, Cannabidiol | 100 | 66.66 |
| Kollidon 90[3] | 10 | 6.66 |
| Polyethylene oxide (1M) | 38.5 | 25.66 |
| Silicon dioxide | 1 | 0.66 |
| Mg stearate | 0.5 | 0.33 |
| Sub weight | 2 × 150 mg | |
| Total weight tablet | 1100 mg | |

[1]Polyaxamer is a nonionic polyoxyethylene-polyoxypropylene block copolymer having a general formula $HO(C_2H_4O)_a(C_3H_6O)_b(C_2H_4O)_aH$, where a and b are positive integers.
[2]Kollidon SR is a polymer blend of piolyvinyl acetate and polyvinylpyrrolidone.
[3]Kollidon 90 is a polyvinylpyrrolidone having a number average molecular weight of about 700,000.

The above description is considered that of the preferred embodiment only. Modifications of the invention will occur to those skilled in the art and to those who make or use the invention. Therefore, it is understood that the embodiment shown in the drawings and described above are merely for illustrative purposes and not intended to limit the scope of the invention, which is defined by the following claims as interpreted according to the principles of patent law, including the doctrine of equivalents.

The invention claimed is:

1. A trilayer tablet comprising: a non-erodible core layer containing at least one pharmaceutically active compound and/or at least one nutritionally active compound; and at least one erodible layer laminated to each side of the non-erodible layer, wherein the non-erodible core layer comprises a combination of a polymer matrix, and a granulation distributed in the matrix, the granulation comprising at least one active compound and a swellable polymer.

* * * * *